(12) United States Patent
Ledden (10) Patent No.: US 11,369,314 B2
(45) Date of Patent: Jun. 28, 2022

(54) BIOFOULING PREVENTION OF WEARABLE SENSORS AND METHODS OF USE AND CALIBRATION RELATED THERETO

(71) Applicant: Siemens Healthcare Diagnostics Inc., Tarrytown, NY (US)

(72) Inventor: David Ledden, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 659 days.

(21) Appl. No.: 16/317,966

(22) PCT Filed: Jun. 7, 2017

(86) PCT No.: PCT/US2017/036314
§ 371 (c)(1),
(2) Date: Jan. 15, 2019

(87) PCT Pub. No.: WO2018/017196
PCT Pub. Date: Jan. 25, 2018

(65) Prior Publication Data
US 2021/0282709 A1   Sep. 16, 2021

Related U.S. Application Data

(60) Provisional application No. 62/363,577, filed on Jul. 18, 2016, provisional application No. 62/363,572, filed on Jul. 18, 2016.

(51) Int. Cl.
*A61B 5/1455* (2006.01)
*A61B 5/00* (2006.01)
(Continued)

(52) U.S. Cl.
CPC ............ *A61B 5/685* (2013.01); *A61B 5/1451* (2013.01); *A61B 5/1459* (2013.01);
(Continued)

(58) Field of Classification Search
None
See application file for complete search history.

(56) References Cited

U.S. PATENT DOCUMENTS 6,743,211 B1 * 6/2004 Prausnitz ........... A61B 5/14514
604/239
8,092,384 B2 * 1/2012 Meyer ................ A61B 5/14546
600/309

(Continued)

FOREIGN PATENT DOCUMENTS

CN   105073179 A   11/2015
CN   105228522 A   1/2016
(Continued)

OTHER PUBLICATIONS

International Search Report and Written Opinion of International Application No. PCT/US2017/036314 dated Sep. 11, 2017.
(Continued)

*Primary Examiner* — Marjan Fardanesh
(74) *Attorney, Agent, or Firm* — Dunlap Codding, P.C.

(57) ABSTRACT

Devices, kits, and methods for (a) determining the presence and/or concentration of at least one analyte(s) of interest present in a patient's fluid sample and devices and methods of calibration related thereto, and (b) preventing, mitigating, and/or eliminating biofouling of an indwelling, wearable biosensor are disclosed and/or claimed herein.

15 Claims, 6 Drawing Sheets

(51) Int. Cl.
    *A61B 5/145*     (2006.01)
    *A61B 5/1459*     (2006.01)
    *A61K 9/00*     (2006.01)
    *A61K 31/192*     (2006.01)
    *A61K 31/573*     (2006.01)
    *A61K 31/616*     (2006.01)
    *A61K 31/722*     (2006.01)

(52) U.S. Cl.
    CPC ........ *A61B 5/14532* (2013.01); *A61B 5/6832* (2013.01); *A61K 9/0021* (2013.01); *A61K 31/192* (2013.01); *A61K 31/573* (2013.01); *A61K 31/616* (2013.01); *A61K 31/722* (2013.01)

(56) References Cited

U.S. PATENT DOCUMENTS

| | | |
|---|---|---|
| 2003/0153900 A1 | 8/2003 | Aceti et al. |
| 2008/0275318 A1 | 11/2008 | Lastovich et al. |
| 2010/0303772 A1 | 12/2010 | McMillan et al. |
| 2011/0081727 A1 | 4/2011 | Colvin, Jr. et al. |
| 2011/0152792 A1 | 6/2011 | Takada |
| 2011/0224515 A1 | 9/2011 | Mir et al. |
| 2013/0046182 A1 | 2/2013 | Hegg et al. |
| 2013/0079605 A1 | 3/2013 | Bandaru et al. |
| 2014/0259652 A1 | 9/2014 | Pushpala et al. |
| 2016/0029937 A1 | 2/2016 | Sia et al. |
| 2016/0045720 A1 | 2/2016 | Suzuki et al. |

FOREIGN PATENT DOCUMENTS

| | | |
|---|---|---|
| JP | 2012520087 A | 9/2012 |
| KR | 20140051648 A | 5/2014 |
| WO | 2008114224 A2 | 9/2008 |
| WO | 2015048777 A1 | 4/2015 |

OTHER PUBLICATIONS

European Search Report and Written Opinion of European Application No. 17831468.8 dated Mar. 25, 2019.
Abraham et al., "Implications of Rising Prediabetes Prevalence", Aug. 2013, Diabetes Care, 36 (8): pp. 2139-2141.
Bantle et al., "Glucose measurement in patients with diabetes mellitus with dermal interstitial fluid", 1997, The Journal of Laboratory and Clinical Medicine, 130 (4): pp. 436-441.
Cengiz et al., "A Tale of Two Compartments: Interstitial Versus Blood Glucose Monitoring", 2009, Diabetes Technology & Therapeutics, 11 Suppl 1: pp. S11-S16.
Loh et al., "Relationship between measured average glucose by continuous glucose monitor and HbA1c measured by three different routine laboratory methods", 2015, Clinical Biochemistry, 48 (7-8): pp. 514-518.
Roe et al., "Bloodless Glucose Measurements", 1998, Critical Reviews in Therapeutic Drug Carrier Systems, 15 (3): pp. 199-241.
Rybicka et al., "The dawn phenomenon and the Somogyi effect—Two phenomena of morning hyperglycaemia", 2011, Endokrynologia Polska/Polish Journal of Endocrinology, 62 (3): pp. 276-283.
Saudek et al., "A New Look at Screening and Diagnosing Diabetes Mellitus", Jul. 2008, J Clin Endocrinol Metab, 93 (7): pp. 2447-2453.
Steck et al., "Early Hyperglycemia Detected by Continuous Glucose Monitoring in Children at Risk for Type 1 Diabetes", Jul. 2014, Diabetes Care, 37: pp. 2031-2033.
Stout et al., "Comparison of Glucose Levels in Dermal Interstitial Fluid and Finger Capillary Blood", 2001, Diabetes Technology & Therapeutics, 3(1): pp. 81-90.
Tabák et al., "Prediabetes: A high-risk state for diabetes development", Jun. 16, 2012, The Lancet, vol. 379: pp. 2279-2290.
Zhou et al., "Relationship between HbA1c and Continuous Glucose Monitoring in Chinese Population: A Multicenter Study", Dec. 2013, PLOS One, 8 (12): pp. 1-6.

\* cited by examiner

BIOFOULING PREVENTION OF WEARABLE SENSORS AND METHODS OF USE AND CALIBRATION RELATED THERETO

CROSS REFERENCE TO RELATED APPLICATIONS

This application claims priority to U.S. Provisional Application No. 62/363,577, filed Jul. 18, 2016 and U.S. Provisional Application No. 62/363,572, filed Jul. 18, 2016. Both disclosures of which are hereby incorporated by reference in their entirety.

STATEMENT REGARDING FEDERALLY FUNDED RESEARCH OR DEVELOPMENT

Not Applicable.

TECHNICAL FIELD

The presently disclosed and/or claimed inventive concept(s) relate to device(s) and method(s) of use and calibration of wearable sensors, including, but not limited to, pre-diabetes wearable sensors. More specifically, the presently disclosed and/or claimed inventive concept(s) relate to wearable sensors configured to reduce and/or eliminate biofouling of such wearable sensors.

BACKGROUND

Numerous devices and methods exist for the continuous detection of analytes that may be present in a patient's fluid sample, including, for instance, a patient's interstitial fluid sample. Such devices, when indwelled within a patient, such as in a patient's stratum corneum or epidermal tissue, have proven to be effective in detecting and continuously monitoring the concentration of analytes indicative of a particular disease or disorder, such as, by way of example only, diabetes. In addition, such devices can be effective in delivering, for instance, drugs and/or other therapeutic compounds when the devices are indwelled within a patient. However, a significant problem exists with such indwelling, wearable sensors—biofouling of the biosensor's microneedles which reduces the accuracy, longevity, and, in some cases, consistent functioning of the biosensor itself. Biofouling refers to the natural phenomenon associated with the wound healing process in which the indwelling sensor and/or its microneedles is/are perceived by the patient's body as a foreign object. As a result, a biological response (such as the wound healing cascade which includes distinct hemostasis, inflammation, proliferation, and maturation phases) is triggered that causes cells and protein(s) (and/or other biological substances) to bind to the microneedles thereby impairing, compromising, and/or destroying biosensor function. Accordingly, there is a current need for improved indwelling, wearable biosensors that mitigate and/or eliminate the detrimental effects of the biofouling process and thereby improve the continuous functioning, active sensing, and wearable duration of the biosensors. Such improved sensors (and methods of use related thereto) may, in one embodiment, comprise a microneedle array that includes at least one microneedle which comprises at least one compound that inhibits the wound healing process. Additionally (or alternatively), the improved indwelling wearable biosensor may also include at least one piezoelectric element that can receive electrical signals from a detector resulting in the at least one piezoelectric element vibrating to thereby dislodge and/or remove any cells, protein(s), and/or other biological substances deposited on or in the microneedles of the biosensor. It is to such improved devices and methods that the presently disclosed and claimed inventive concept(s) is/are directed.

DETAILED DESCRIPTION

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references which may be cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "anti-wound healing compound(s)" includes any compound(s), substance(s), or combinations thereof that mitigate, inhibit, and/or eliminate the wound healing process and/or cascade. Examples of anti-wound healing compound(s) include, but are not limited to, immunosuppressant compounds, corticosteroids, chitosan, nonsteroidal anti-inflammatory drugs, including, without limitation, aspirin, naproxen, and/or ibuprofen, and anticoagulant compounds, and combinations thereof. The anti-wound healing compound(s) can be incorporated on or in each, some, or all of the microneedles of the microneedle array, including, but not limited to, via coating the anti-wound healing compounds on a surface or multiple surfaces of each, some, or all of the microneedles of the microneedle array. Alternatively, or in addition to, the anti-wound healing compound(s) can be impregnated within the polymeric materials forming the microneedles during the manufacturing process of the microneedle array.

As used herein, the term "biofouling" means the accumulation and/or agglomeration of cells, protein(s) and/or other biological substances on at least one surface of and/or in the microneedle(s) of the microneedle array of the indwelling, wearable biosensor such that the functioning of the biosensor is impaired, compromised, and/or eliminated. Such cells, protein(s), other biological substances, include, but are not limited to, fibrin, fibronectin, glycoprotein, growth factors, kinins, cytokines, chemokines, fibroblasts, platelets, pro-inflammatory factors, including, without limitation, serotonin, bradykinin, prostaglandins, prostacyclins, thromboxane, and histamine, proteases, macrophages, monocytes, phagocytes, vasoactive amines, eicosanoids, leukocytes, and neutrophils (including polymorphonuclear neutrophils).

The term "circuitry" as used herein may be analog and/or digital components, or one or more suitably programmed processors (e.g., microprocessors) and associated hardware and software, controller(s), or hardwired logic. Also, a "component" may perform one or more functions. The term "component" may include hardware, such as a processor (e.g., microprocessor) and application specific integrated circuit (ASIC), field programmable gate array (FPGA), a combination of hardware and software, and/or the like. The term "processor" as used herein means a single processor or multiple processors working independently or together to collectively perform a task.

The term "fluid sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperitoneal fluid, cystic fluid, sweat, interstitial fluid, tears, mucus, urine, bladder wash, semen, combinations, and the like. In one non-limiting embodiment, the fluid sample utilized in accordance with the presently disclosed and/or claimed inventive concept(s) is interstitial fluid.

The term "patient" includes human and veterinary subjects. In certain embodiments, a patient is a mammal. In certain other embodiments, the patient is a human, including, but not limited to, infants, toddlers, children, young adults, adults, and elderly human populations. "Mammal" for purposes of treatment refers to any animal classified as a mammal, including human, domestic and farm animals, nonhuman primates, and zoo, sports, or pet animals, such as dogs, horses, cats, cows, etc.

The terms "piezoelectric," "piezoelectricity," and/or "piezoelectric effect" mean the ability of certain materials to generate an electric charge in response to mechanical stress and/or changes in pressure. In addition, these terms encompass the reverse (i.e., reverse piezoelectric effect) meaning that such materials stretch, compress, and/or vibrate when exposed to an electrical field, electrical signal, or electrical input. Examples of piezoelectric materials/elements included, but are not limited to, quartz, Berlinite, topaz, tourmaline, cane sugar, Rochelle salt, barium titanate, and lead zirconate titanate.

The term "wireless communication" means data communication that is performed and delivered wirelessly and incorporates all procedures and forms of connecting and communicating between two or more devices using a wireless signal through wireless communication technologies and devices. The term wireless communication includes, but is not limited to satellite, mobile, wireless network, infrared, and Bluetooth communications.

Turning now to particular embodiments, the presently disclosed and claimed inventive concept(s) relate to a device(s) and method(s) for mitigating and/or eliminating biofouling of the microneedle array thereby improving the performance and longevity of a biosensor. While a patient's fluid test sample is primarily discussed herein in the context of a patient's interstitial fluid sample, it should be readily understood by a person having ordinary skill in the art that the presently disclosed and/or claimed inventive concepts have applications to all types of a patient's fluid sample. In addition, while the majority of examples described herein refer to the detection and continuous monitoring of glucose, a person having ordinary skill in the art should readily understand that the presently disclosed and/or claimed inventive concept(s) are not limited to only glucose detection, but can be utilized for the detection and monitoring of any number or types of analytes which may be present in the patient's fluid sample. More specifically, the presently disclosed and claimed inventive concept(s) relate to embodiments of an improved indwelling, wearable biosensor and methods of use related thereto that mitigate or eliminate the effects of biofouling.

It is contemplated that virtually any reagent used in the fields of biological, chemical, or biochemical analyses and assays could be used in the devices and methods of the presently claimed and disclosed inventive concept(s) as a sensor for detecting an analyte of interest present in a patient's fluid sample. It is contemplated that these reagents may undergo physical and/or chemical changes when bound to an analyte of interest whereby the intensity, color, nature, frequency, fluorescence, wavelength or type of signal generated by the reagent-analyte complex is directly proportional or inversely proportional to the concentration of the analyte existing within the patient's fluid sample. These reagents may contain or comprise indicator dyes, metal, enzymes, fluorophores, polymers, antibodies, and electrochemically reactive ingredients and/or chemicals that, when reacting with an analyte(s) of interest, may exhibit a change in color, fluorescence or wavelength. In one embodiment, the reagent (which acts as an analyte sensor(s)) comprises a fluorophore(s) and/or fluorescent dye(s) that is/are associated with the polymeric material(s) on at least one outside surface(s) of each microneedle, within each microneedle (including, but not limited to, within the tip portions of each microneedle), or both on the outside of and within each microneedle of the microneedle array. The fluorophore(s) and/or fluorescent dye(s) comprising the analyte sensor(s) can be associated with the polymeric material(s) either on the outside surface(s) of each microneedle or within the tip(s) of each microneedle of the microneedle array. Such fluorophores and fluorescent dyes include, but are not limited to fluorescein, rhodamine, eosin, Oregon Green, Texas Red, coumarin derivatives, cyanine, indocarbocyanine, oxacarbocyanine, thiacarbocyanine, merocyanine, squaraine derivatives, pyridyoxazole, nitrobenzoxadiazole, benzoxadiazole, anthraquinones, pyrene derivatives, Nile Red, Nile Blue, cresyl violet, oxazine, proflavin, acridine orange, acridine yellow, auramine, crystal violet, malachite green, porphin, phtalocyanine, bilirubin, boronate, and combinations thereof. In one non-limiting embodiment, the reagent is a boronate fluorophore.

The presently disclosed and/or claimed inventive concept(s) can detect certain conditions associated with a patient's fluid sample, including, but not limited to, a sample's specific gravity, concentration, and/or pH. As disclosed herein, the device(s), kit(s), and method(s) disclosed and/or claimed herein may be used for the analysis of any fluid sample of a patient, including, without limitation, whole blood, plasma, serum, urine, or interstitial fluid. In one non-limiting embodiment, the fluid sample of the patient is interstitial fluid.

In one embodiment, the analyte sensor(s) comprise at least fluorophore that is covalently associated to the polymeric material(s) that form the microneedles of the microneedle array. The analyte sensor(s), when comprising at least one fluorophore, primarily functions on the principle of photo-induced electron transfer. In the absence of an analyte of interest in a patient's fluid sample (for instance, glucose), the nitrogen of the amine group of the fluorophore sensor acts as an electron-rich center and the fluorophore is quenched. However, in the presence of an analyte(s) of interest (for instance, glucose), the analyte molecules bind to the fluorophore sensor(s) thereby inhibiting the quenching effect and resulting in the emittance of fluorescent light, the intensity of which is directly proportional to the concentration of the analyte of interest. As further discussed herein, the microneedle array may additionally comprise at least one calibration needle. Unlike the other microneedles comprising the microneedle array, the analyte sensor(s) comprising the at least one calibration microneedle is/are not activated by at least one analyte present in the patient's fluid sample; rather, the analyte sensor(s) of the at least one calibration needle is always "on," continually and constantly emitting a signal (for instance, when the analyte sensor(s) comprise at least on fluorophore, the analyte sensor(s) emit a continuous and constant fluorescent signal), the intensity of which is indicative of a known and/or pre-calculated concentration of the analyte(s) of interest.

Figure 1:
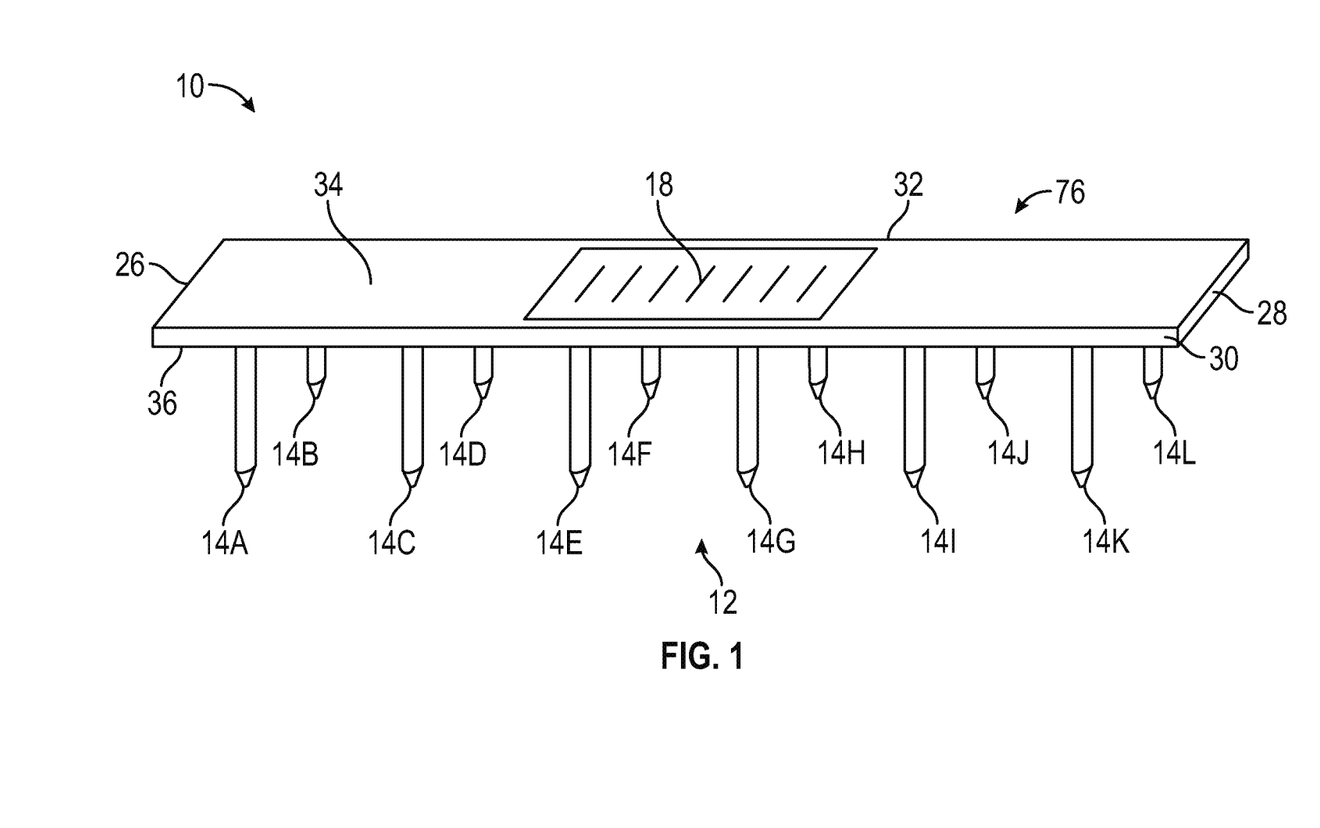
FIG. 1 is a perspective side view of one embodiment of the presently disclosed and/or claimed improved indwelling, wearable biosensor.

Referring now to the Figures, and more particularly to FIG. 1, shown therein is an embodiment of the presently disclosed and/or claimed improved indwelling, wearable biosensor 10. The biosensor 10 comprises a microneedle array 12, a substrate 16, and a detector 18.

The microneedle array 12 comprises a plurality of microneedles 14A-14L. While shown in FIG. 1 as comprising twelve (12) microneedles, it should be readily understood by a person having ordinary skill in the art that the microneedle array 12 can comprise any number of microneedles that accomplishes the presently disclosed and/or claimed inventive concept(s). By way of example only, and not by way of limitation, the microneedle array 12 can comprise 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or greater than 1000 microneedles. The microneedles 14A-14L can be constructed of any material capable of accomplishing the presently disclosed and/or claimed inventive concept(s). Such materials are generally thermally stable, biologically and chemically compatible, safe, flexible, non-hygroscopic, inert, and optically transparent. Such materials include, but are not limited to, polymeric material(s), such as, by way of example only, polyacrylamide, poly(methyl vinyl ether-alt-maleic anhydride) (PMVE/MA), maltose, carboxymethylcellulose, amylopectin, sodium hyaluronate, chondroitin sulphate/dextrin, sodium alginate, hydroxypropyl cellulose, PMVE/MA-poly (ethylene glycol), polyvinyl alcohol (PVA), PVA-dextrin, poly(lactic-go-glycolic) acid (PLGA), polylactic acid, polyglycolic acid, polycarbonate, polystyrene, polydimethylsiloxane (PDMS), and/or combinations thereof. In one non-limiting embodiment, the microneedles 14A-14L are constructed of polyacrylamide.

The dimensions of the microneedles 14A-14L can be the same, different, or combinations thereof, provided that the microneedles 14A-14L are able to pierce and reside in the patient's epidermal tissue such that they remain in continuous contact with the patient's fluid sample. Typically, the microneedles 14A-14L have dimensions of: (1) a length of equal to or less than 150 micrometers, or from about 300 to about 1,500 micrometers, or from about 400 to about 1,400 micrometers, or from about 500 to about 1,300 micrometers, or from about 600 to about 1,200 micrometers, or from about 700 to about 1,100 micrometers, or from about 800 to about 1,000 micrometers, or about 900 micrometers; (2) a width from about 100 to about 500 micrometers, or from about 200 to about 450 micrometers, or from about 250 to about 400 micrometers, or from about 300 to about 350 micrometers; and (3) a thickness from about 15 to about 100 micrometers or from about 25 to about 90 micrometers, or from about 35 to about 80 micrometers, or from about 45 micrometers to about 70 micrometers, or from about 55 to about 60 micrometers. In addition and as discussed further with respect to FIGS. 2A and 2B, at least a portion, including, without limitation, a tip portion, of the microneedles 14A-14L are impregnated and/or coated (via association with the polymeric material forming each of the microneedles 14A-14L) with at least one anti-wound healing compounds (as shown in FIG. 3) that mitigates and/or eliminates biofouling when the microneedles 14A-14L are indwelled within a patient's stratum corneum or epidermal tissue and in contact with the patient's fluid sample. As discussed further with respect to FIGS. 2A and 2B, each of the microneedles 14A-14L of the microneedle array 12 contain and/or are coated with at least one fluorophore sensor that is associated with the polymeric material forming each of the microneedles 14A-14L of the microneedle array 12. Accordingly, in the presence of an analyte(s) of interest (for instance, glucose), the fluorophore sensor(s) emit a fluorescent signal(s) indicative of and/or directly proportional to the concentration of the analyte(s) of interest in the patient's fluid sample. Such fluorescent signal(s) are received by the detector 18 (discussed in greater detail herein) which interprets and correlates the specific fluorescent signal(s) to the concentration of the analyte(s) of interest present within the patient's fluid sample.

The indwelling, wearable biosensor 10 further comprises a substrate 16, which, in one non-limiting embodiment, comprises a first end 26, a second end 28, a first side 30, a second side 32, a top portion 34, and a bottom portion 36. While shown in FIG. 1 as being substantially rectangular in shape, it should be readily understood to a person having ordinary skill in the art that the substrate 16 can be any shape conducive for accomplishing the presently disclosed and/or claimed inventive concept. Such shapes include, but are not limited to, a circle, triangle, square, diamond, pentagon, hexagon, heptagon, octagon, nonagon, decagon, rhombus, trapezoid, rhombus, and parallelogram.

The substrate 16 is preferably constructed of a durable, flexible, ultrathin, lightweight, stretchable, "skin-like" membrane(s) that conformably adhere and/or laminate onto the surface of a patient's skin via soft contact—similar to that of well-known adhesive bandages and/or transdermal patches. In one embodiment, the bottom portion 36 of the substrate 16 comprises an adhesive material (not shown) for securing the biosensor 10 to the patient's skin. Alternatively, the biosensor 10 may be adhered and secured to the patient's skin solely via van der Waals interactions between the substrate 16 and the patient skin; however, it should be readily understood by a person having ordinary skill in the art that the substrate 16 may be secured to the patient's skin via any manner commonly known in the art. Such durable, flexible materials may include, but are not limited to, woven fabric, plastic, such as polyvinyl chloride (PVC), polyethylene, and/or polyurethane, poly(dimethylsiloxane) (PDMS), or latex, and/or combinations thereof. Such adhesive materials may include, but are not limited to, an acrylate substance, including, without limitation, methacrylates and epoxy diacrylates/vinyl resins, and/or combinations thereof. Preferably, the substrate 16 is a tape or film in which the adhesive (not shown) firmly secures the microneedles 14A-14L of microneedle array 12 in positions along the bottom portion 36 of the substrate 16. Accordingly, each of the microneedles 14A-14L of the microneedle array 12 remain firmly and/or permanently secured to or through the bottom portion 36 of the substrate 16 when such microneedles 14A-14L are indwelled within the stratum corneum or epidermal tissue of the patient. Such methods and manners for securing the microneedles 14A-14L of the microneedle array 12 are commonly known in the art. While shown in FIG. 1 as being uniformly spaced along the bottom portion 36 of the substrate 16, it should be readily understood by a person having ordinary skill in the art that the microneedles 14A-14L can be positioned in any configuration capable of accomplishing the presently disclosed and/or claimed inventive concept(s). For instance, the microneedles 14A-14L (or more or less microneedles as contemplated herein) can be positioned randomly or in any predetermined configuration upon or through the bottom portion 36 of the substrate 16.

The indwelling, wearable biosensor 10 further comprises a detector 18 that receives the fluorescent signal(s) emitted by the fluorophore sensor(s) (as shown in greater detail in FIGS. 2A and 2B) contained within and/or coated on each of the microneedles 14A-14L of the microneedle array 12. Accordingly, in one embodiment, the detector 18 comprises a fluorometer, including, without limitation, a microfluorometer, a filter fluorometer or a spectrofluorometer. As shown FIG. 1, in one non-limiting embodiment, the detector 18 is located on (and, in one embodiment, may be permanently affixed to) the top portion 34 of the substrate 16; however, it should be understood by a person having ordinary skill in the art that the detector 18 may be located on any portion of the substrate 16 provided that the detector 18 is capable of receiving the fluorescent signal(s) emitted by the fluorophore sensor(s) (shown in more detail in FIGS. 2A and 2B) contained within and/or coated on each of the microneedles 14A-14L of the microneedle array 12.

Figure 5:
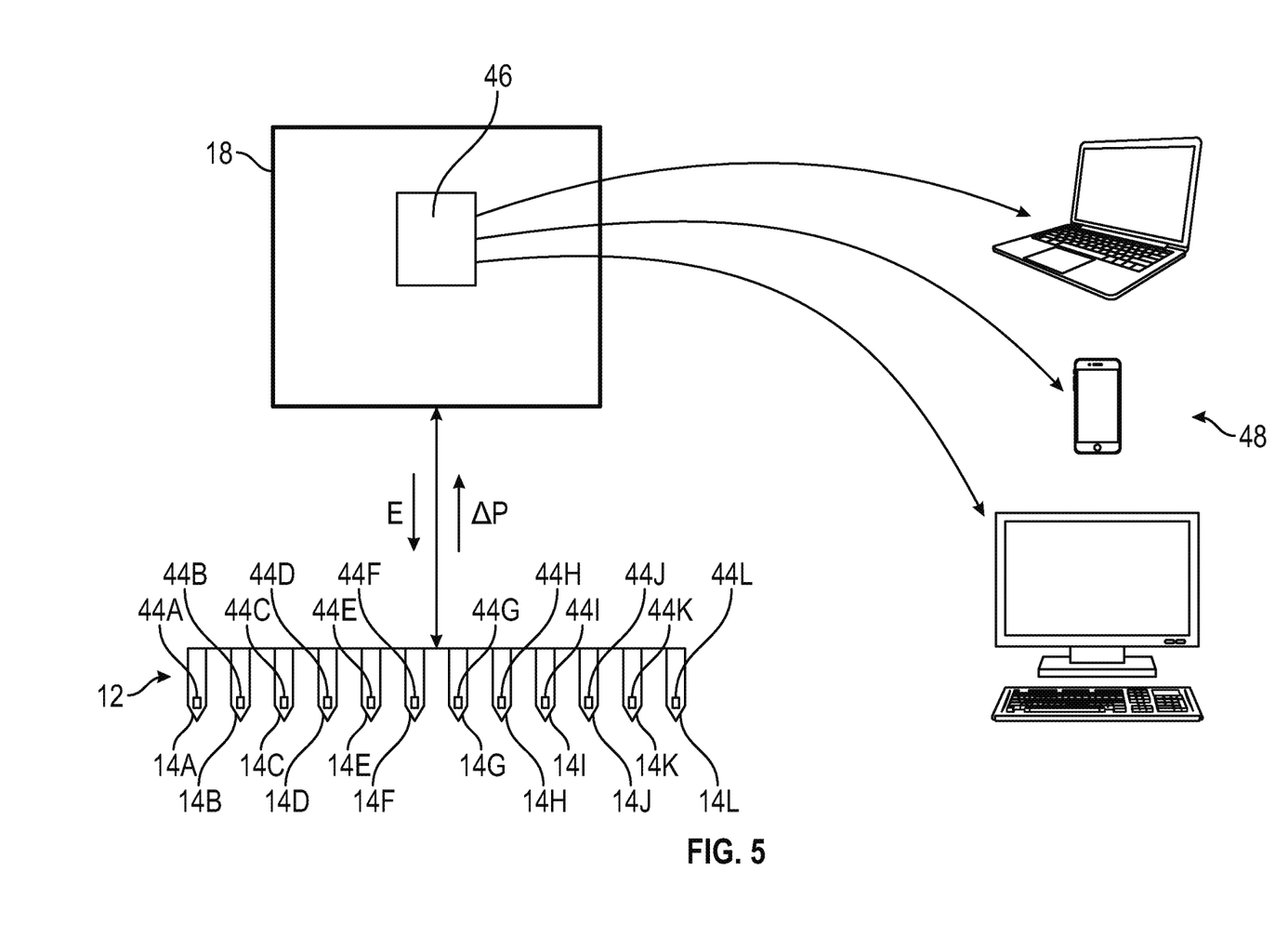
FIG. 5 is a schematic diagram depicting an alternative embodiment of the presently disclosed and/or claimed inventive concept(s) comprising a piezoelectric element for preventing, mitigating, and/or eliminating biofouling of the biosensor.

As discussed more specifically hereinbelow (and as shown in FIG. 5), the detector 18 comprises circuitry (including, without limitation, controller(s), microprocessor(s), memory, and/or interface(s)) that allows the detector 18 to: (a) correlate and calculate the concentration of at least one analyte(s) of interest based on the signal(s) received by the analyte sensor(s); and (b) wirelessly communicate with at least one external device such that the data (including, without limitation, fluorescence and calculated concentration) collected by the detector 18 can be wirelessly communicated to such at least one external device. Thereafter, a user (including, without limitation, a doctor, nurse, or person responsible for administering care to the patient (including the patient himself/herself) can interpret, monitor, and develop effective therapeutic plans for treating the patient based on the display of such data on such at least one external device.

The biosensor 10 is configured such that the microneedle array 12 and the detector 18 are proximally positioned to one another via connection with or through the substrate 16. As a result of this close proximity, fluorescent signal loss received by the detector 18 from the fluorophore sensor(s) (shown in more detail in FIGS. 2A and 2B) contained within and/or coated on each of the microneedles 14A-14L of the microneedle array 12 is mitigated, minimized, and/or eliminated—thereby resulting in a more accurate detection of the concentration of an analyte(s) of interest contained within the patient's fluid sample.

Figure 1A:
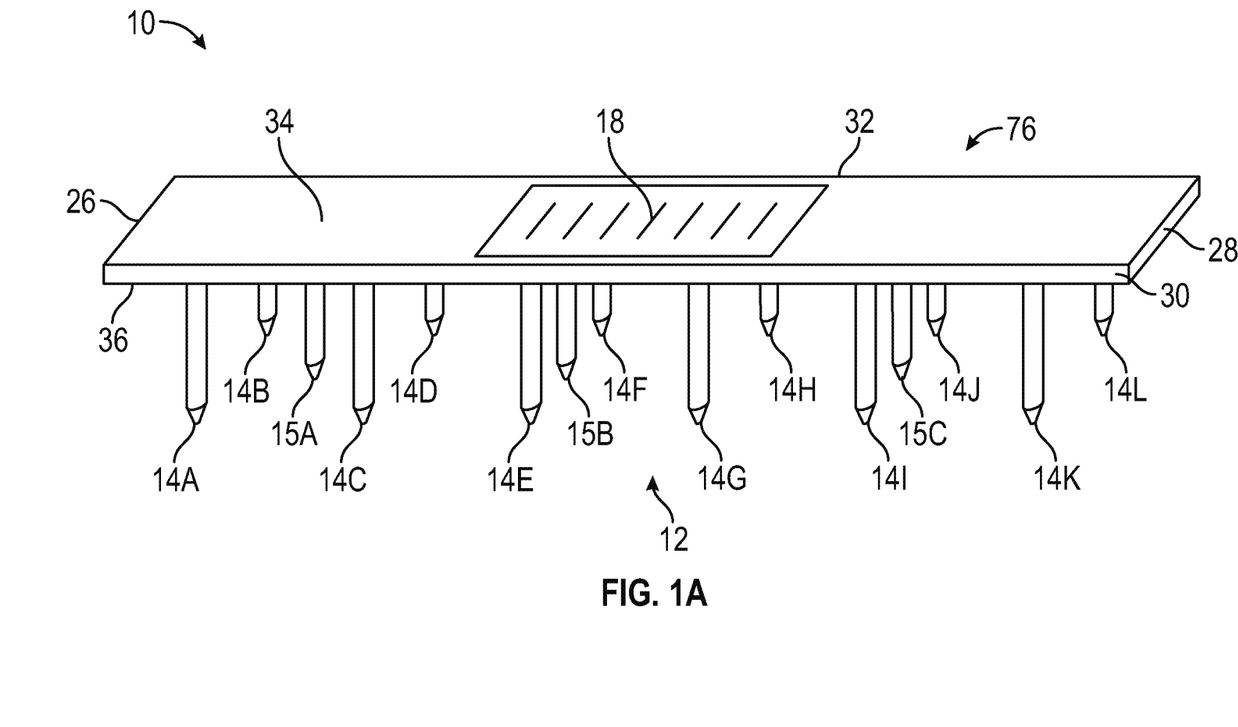
FIG. 1A is a perspective side view of an additional embodiment of the indwelling, wearable biosensor of FIG. 1 which further comprises a plurality of calibration microneedles.

Referring now to FIG. 1A, shown therein is a non-limiting additional embodiment of the indwelling, wearable biosensor 10 of FIG. 1, wherein the microneedle array 12 of biosensor 10 further comprises a plurality of calibration microneedles 15A-15C. While shown in FIG. 1A as comprising three calibration microneedles 15A-15C, it should be readily understood to a person having ordinary skill in the art that the microneedle array 12 can comprise any number of calibration microneedles (including, without limitation, a single calibration microneedle) and such calibration microneedles can be oriented in any configuration that accomplishes the presently disclosed and/or claimed inventive concept(s). For purposes of simplicity, the description of the biosensor 10 will not be repeated herein, as the only difference(s) from the embodiments described with respect to FIG. 1 and FIG. 1A is the inclusion and functioning of the plurality of calibration microneedles 15A-15C.

The plurality of calibration microneedles 15A-15C are similarly structured and constructed as microneedles 14A-14L in that each of calibration microneedles 15A-15C comprise a fluorophore sensor(s) (not shown, but which are associated with the polymeric material(s) forming the calibration microneedles 15A-15C) that emit fluorescent signal(s) indicative of at least a concentration of an analyte(s) of interest (such as, by way of example only, glucose) which may be present in a patient's fluid sample. However, the fluorophore sensor(s) of the calibration needles 15A-15C are always active (i.e., they are not separately activated by the binding of an analyte(s) of interest to the fluorophore sensor(s)) and, consequently, constantly emit fluorescent signals which can be received by the detector 18. The constant fluorescent signals emitted by fluorophore sensor(s) of the calibration microneedles 15A-15C can be pre-calibrated and/or pre-selected to emit fluorescent signals at intensities that are indicative of a known concentration of an analyte(s) of interest. Such intensities (and accordingly, the known concentrations) can be the same, different, or a combination of same and different for each fluorophore sensor(s) of the calibration microneedles 15A-15C. Accordingly, the concentration of the analyte(s) of interest (for instance, glucose) being actively sensed by microneedles 14A-14L can be accurately calculated by the detector 18 by comparing such fluorescent signal(s) to the constant fluorescent signals emitted by the fluorophore sensor(s) of the calibration microneedles 15A-15C. In addition, the calibration microneedles 15A-15C can further be utilized to detect whether biofouling of the microneedles 14A-14L is occurring, as the detector 18 would be able to detect changes in the fluorescent signal(s) emitted by the fluorophore sensor(s) of microneedles 14A-14L as compared to the constant fluorescent signal(s) emitted by the fluorophore sensor(s) of the calibration needles 15A-15C. If biofouling is detected, appropriate remediation can be accomplished in accordance with the presently disclosed and/or claimed inventive concept(s) and as described herein.

Figure 2A:
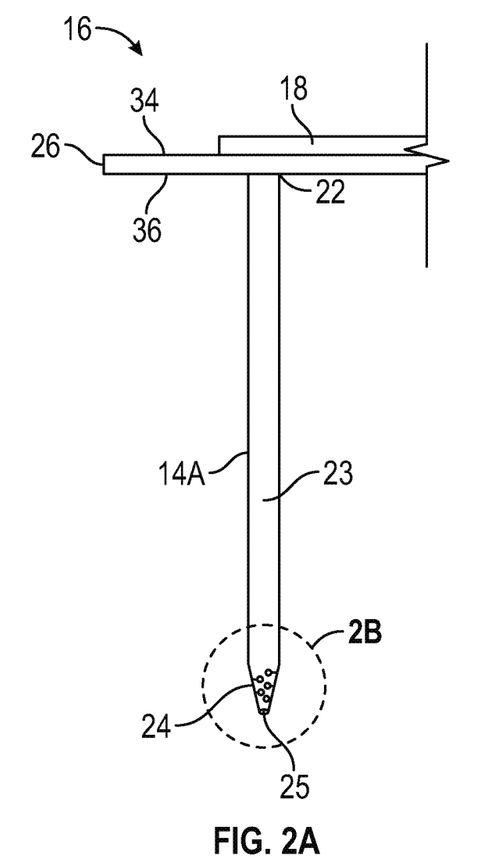
FIG. 2A is an elevational side view of one embodiment of an improved microneedle of the presently disclosed and/or claimed improved indwelling, wearable biosensor.
Figure 2B:
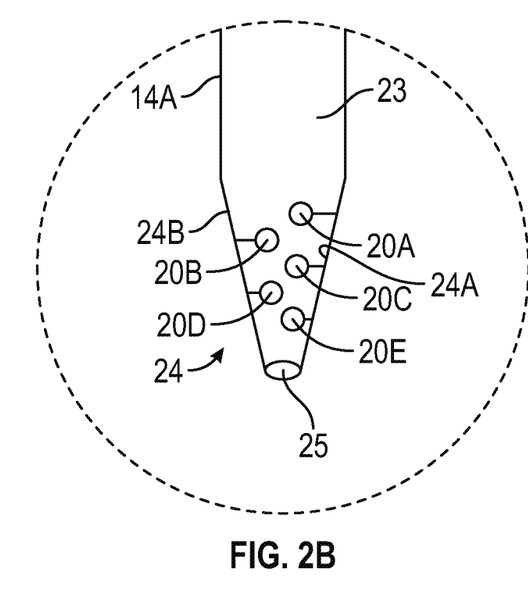
FIG. 2B is a detailed elevational side view of one embodiment of a tip portion of the improved microneedle of the presently disclosed and/or claimed improved indwelling, wearable biosensor depicted in FIG. 2A in which the fluorophore sensor(s) are further illustrated.
Figure 3:
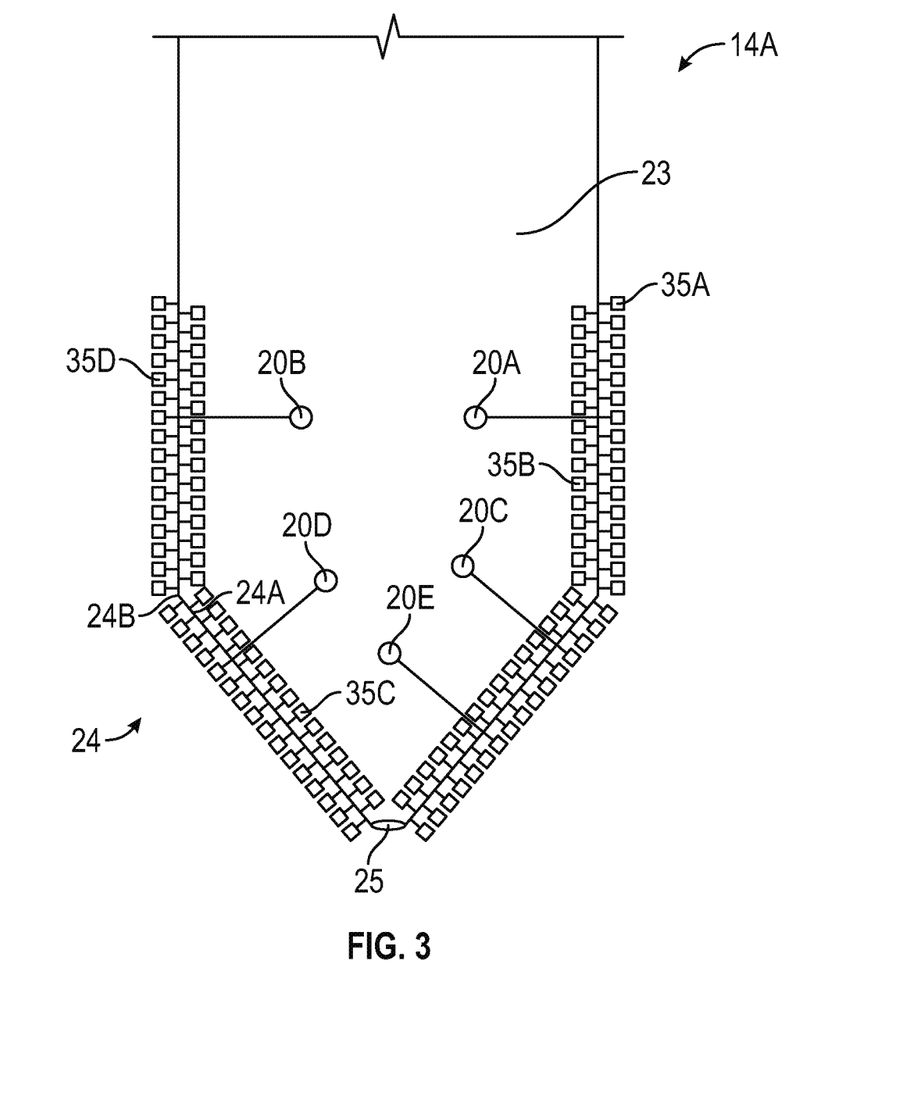
FIG. 3 is a detailed schematic of one embodiment of a tip portion of the improved microneedle of the presently disclosed and/or claimed inventive concept(s) in which at least one anti-wound healing compound(s) is associated with the polymeric material forming the microneedle such that the anti-wound healing compound(s) is coated on at least one surface of the microneedle to prevent, mitigate, and/or eliminate biofouling of the biosensor.

Referring now to FIGS. 2A and 2B, shown therein is an embodiment of an improved microneedle 14A of the presently disclosed and/or claimed inventive concept(s). While FIGS. 2A and 2B show a single microneedle 14A, as discussed hereinabove, it should be readily understood to a person having ordinary skill in the art that the microneedle array 12 can comprise any number of microneedles that accomplishes the presently disclosed and/or claimed inventive concept(s). However, for purposes of illustration and simplicity, only one microneedle 14A is shown in FIGS. 2A and 2B. The following description with respect microneedle 14A is equally applicable to any and all microneedles comprising the microneedle array 12, including, for example, microneedles 14A-14L.

Referring now to FIG. 2A, the microneedle 14A comprises a base portion 22, a tip portion 24, a bore 23 extending the length of the microneedle 14A from the base portion 22 to the tip portion 24, and an opening 25 at a distal end of the bore 23 of the tip portion 24. While microneedle 14A is depicted in FIG. 2A (and FIGS. 2B, 3, and 4) as comprising an opening 25, it should be readily understood by a person having ordinary skill in the art that presently disclosed and/or claimed inventive concept(s) is/are not limited to this embodiment. For instance, in one non-limiting embodiment, microneedle 14A may be formed of a porous hydrogel (including, but not limited to, polyacrylamide). In this embodiment, opening 25 is not necessary as the patient's fluid sample is capable of diffusing through and in the porous hydrogel forming microneedle 14A whereby at least one analyte(s) of interest contained within the patient's fluid sample associates with the at least one analyte sensor(s) associated with and/or polymerized and/or impregnated in the microneedle 14A.

As shown in FIG. 2A and as discussed herein, the base portion 22 of microneedle 14A is firmly secured to the bottom portion 36 of the substrate 16. In one embodiment, the securement of the base portion 22 of microneedle 14A to the bottom portion 36 of the substrate 16 may be accomplished via any mechanism commonly known in the art, including, but not limited to, via adhesive(s) or seamless integration during the manufacturing process of the biosensor 10. In an alternative non-limiting embodiment, microneedle 14A is firmly secured via direct integration in or attachment to the detector 18 (i.e., through the substrate 16), such that fluorescent signal(s) generated and emitted by the fluorophore sensor(s) in response to the detection of an analyte(s) of interest in a patient's fluid sample is directly transmitted through the bore 23 to the detector 18 (thereby mitigating signal loss). In another alternative non-limiting embodiment, the substrate 16 comprises pre-formed openings (not shown) throughout the substrate 16. The microneedle 14A (and any and all microneedles comprising the microneedle array 12) can be cast through the substrate 16, such that a portion of the material forming microneedle 14A is present on the top portion 34 of the substrate thereby forming a securing rim for securing microneedle 14A in and through the substrate 16. In this embodiment, microneedle 14A forms around a cast (not shown) in which the cast can be any structure and shape conducive for forming microneedle 14A (and any and all microneedles of the microneedle array 12). In one non-limiting embodiment, the cast can be at least one wire or inert rod which can be removed from the microneedle 14A following the formation of microneedle 14A, including, but not limited to, via pulling the cast from the microneedle 14A and the substrate 16 after the formation of microneedle 14A.

Referring now to FIG. 2B, shown therein is a detailed view of the tip portion 24 of microneedle 14A depicted in FIG. 2A. The tip portion 24 of microneedle 14A includes a plurality of analyte sensor(s) 20A-20E which is/are associated with the polymeric material of which microneedle 14A is constructed. As the analyte sensor(s) 20A-20E is/are associated with such polymeric material(s), the analyte sensor(s) 20A-20E can be associated within the tip portion 24 of microneedle 14A (for instance, as shown in FIG. 2B, on at least one inner surface 24A of the tip portion 24 of microneedle 14A) or, alternatively (or additionally), on at least outer surface 24B of the tip portion 24 of microneedle 14A. In an alternative non-limiting embodiment, the analyte sensor(s) 20A-20E may be separately included in the polymeric material used to construct microneedle 14A, such that, upon polymerization of microneedle 14A, the analyte sensor(s) 20A-20E are disposed within the polymeric material forming microneedle 14A. Accordingly, in this embodiment, analyte sensor(s) 20A-20E are disposed within the entire structure of microneedle 14A and are not limited to just the tip portion 24 of microneedle 14A. While five analyte sensor(s) 20A-20E are depicted in FIG. 2B, it should be readily understood to a person having ordinary skill in the art that any number of analyte sensor(s) can be utilized to accomplish the presently disclosed and/or claimed inventive concept(s). As discussed previously hereinabove, when such analyte sensor(s) comprise at least one fluorophore, such at least one fluorophore sensor(s) and/or fluorescent dyes include, but are not limited to, fluorescein, rhodamine, eosin, Oregon Green, Texas Red, coumarin derivatives, cyanine, indocarbocyanine, oxacarbocyanine, thiacarbocyanine, merocyanine, squaraine derivatives, pyridyoxazole, nitrobenzoxadiazole, benzoxadiazole, anthraquinones, pyrene derivatives, Nile Red, Nile Blue, cresyl violet, oxazine, proflavin, acridine orange, acridine yellow, auramine, crystal violet, malachite green, porphin, phtalocyanine, bilirubin, and boronate. In one non-limiting embodiment, the at least one analyte sensor(s) comprise a boronate fluorophore.

While the fluorophore sensor(s) 20A-20E can be adapted to detect any analyte(s) of interest that may be present in a patient's fluid sample, for purposes of illustration, the analyte sensor(s) 20A-20E are described hereinbelow with respect to the detection of glucose in the patient's fluid sample. In one non-limiting embodiment, the analyte sensor(s) 20A-20E comprises a molecule composed of a glucose receptor reporting a fluorophore and a monomer conjugation site. In this embodiment, the entire analyte sensor(s) 20A-20E are associated with the polymeric material forming the microneedle 14A, and, more specifically, as shown in FIG. 2B, at least one inner portion 24A of the tip portion 24 of microneedle 14A. The analyte sensor(s) 20A-20E, when comprising at least one fluorophore, operate(s) on the principle of induced electron transfer. For instance, in the absence of glucose, nitrogen of the amine group comprising the receptor of the analyte sensor(s) 20A-20E acts as an electron-rich center thereby quenching the fluorophore via electron transfer from the receptor. However, in the presence of glucose, glucose molecules bind to the glucose receptor and the redox state of the glucose receptor is altered. As a result, quenching of the fluorophore via electron transfer is inhibited resulting in the emittance of fluorescent light from the fluorophore, the intensity of which is directly proportional to the concentration of glucose (or the particular analyte(s) of interest being monitored). In this embodiment, the fluorescent light emitted by the fluorophore(s) of the analyte sensor(s) 20A-20E propagate through the optically transparent polymeric material forming microneedle 14A (for instance, either through the polymeric material itself or up through bore 23 of microneedle 14A) where it is received by detector 18. In an alternative, non-limiting embodiment, at least one portion of microneedle 14A can comprise at least one reflective cladding material, at least one reflective cladding materials facilitating the propagation of the signals emitted by the analyte sensor(S) 20A-20E (for instance, when the analyte sensor(s) comprise at least one fluorophore, a fluorescent signal(s)) through bore 23 of microneedle 14A to detector 18. In one non-limiting embodiment, the at least one reflective cladding material comprises metallic silver, the metallic silver being applied to at least one portion of the microneedle 14A via dipping microneedle 14A in a solution containing the metallic silver or via spraying the metallic silver on at least one portion of microneedle 14A. Detector 18 than correlates and calculates the concentration of glucose present in the patient's fluid sample based on the intensity of the fluorescent signal(s) received from the analyte sensor(s) 20A-20E. Subsequently, and as discussed further with respect to FIG. 5, the detector wirelessly communicates the correlated fluorescence/concentration information to at least one external device for display and further analysis. Thereafter, a user (including, without limitation, a doctor, nurse, or person responsible for administering care to the patient, including the patient himself/herself) can interpret, monitor, and develop effective therapeutic plans for treating a patient based on the display of such data on such external devices. The detector 18 can be programmed to receive the fluorescent signals from the analyte sensor(s) 20A-20E at predetermined intervals (for instance, by way of example only, every 1, 2, or 5 minutes) or, alternatively, the detector can continuously receive such fluorescent signals. Accordingly, the detector 18 can correlate and calculate the fluorescence/concentration data and/or wirelessly communicate such data at pre-determined interval or continuously.

The affinity of the analyte sensor(s) 20A-20E for glucose is low enough to allow for dynamic sensing and, when glucose is the analyte being monitored, it/they possess a binding affinity for D-glucose over other carbohydrates. Such binding affinity is strong enough to detect low levels of glucose present in a patient's fluid sample, especially when such patient's fluid sample is interstitial fluid.

Referring now to FIG. 3, shown therein is one non-limiting embodiment of the presently disclosed and/or claimed inventive concept(s) in which the tip portion 24 of microneedle 14A is coated with an anti-wound healing compound(s) to prevent, mitigate, and/or eliminate the biofouling process. Solely for the purposes of simplicity, non-limiting examples of the anti-wound healing compound(s) are depicted in FIG. 3 as distinct reference numerals 35A, 35B, 35C, and 35D. However, it should be readily understood to a person having ordinary skill in the art that any number or combination of anti-wound healing compound(s) can be used to accomplish the objective(s) of the presently disclosed and/or claimed inventive concept(s). Moreover, the anti-wound healing compound(s), including anti-wound healing compound(s) 35A-35D, of the presently disclosed and/or claimed inventive concept(s) may comprise the same, different, or combinations of same and different compounds, drugs, and/or compositions. In addition, while only the tip portion 24 of microneedle 14A is depicted in FIG. 3, it should be readily understood to a person having ordinary skill in the art that the following description with respect to the anti-wound healing compound(s) applies equally to each of the microneedles comprising the microneedle array 12 of the indwelling, wearable biosensor 10. In addition, while FIG. 3 depicts anti-wound healing compound(s) 35A-35D as being substantially located on and in the tip portion 24 of microneedle 14A, a person having ordinary skill in the art should readily appreciate that anti-wound healing compound(s) 35A-35D (and any anti-wound healing compound(s) of the presently disclosed and/or claimed inventive concept(s)) can be located in and/or on any portion of microneedle 14A, including, without limitation, in and/or on the entire length of microneedle 14A.

When the microneedle 14A is indwelled within the epidermal tissue of a patient, the wound-healing process is triggered due to the patient's body perceiving microneedle 14A (and any and all microneedles of the microneedle array 12) as foreign objects. As a result, a biological response (such as the wound healing cascade) is triggered that resulting in cells, protein(s) and/or other biological substances to bind to and/or clog microneedle 14A (especially tip portion 24A), thereby impairing, compromising, and/or destroying the functioning of the indwelling, wearable biosensor 10—a process known as biofouling.

In one embodiment, as shown in FIG. 3, the effects of biofouling can be prevented, mitigated, and/or eliminated by associating at least one anti-wound healing compound(s) 35A-35D on at least one inner surface 24A and at least one outer surface 24B of the tip portion 24 of microneedle 14A. While shown in FIG. 3 as being associated only with the inner surface 24A and outer surface 24B of the tip portion 24, it should be readily understood by a person having ordinary skill in the art that anti-wound healing compound(s) 35A-35D can be associated with any surface(s) of microneedle 14A and are not limited to only the tip portion 24. The at least one anti-wound healing compound(s) 35A-35D can be associated with a surface of microneedle 14A via any method commonly known in the art, including, but not limited to, applying the at least one anti-wound healing compound(s) 35A-35D to the tip portion 24 of microneedle 14A (and/or to any portion or the entirety of microneedle 14A) via submersion, dipping, and/or spraying. In an additional embodiment, the at least one anti-wound healing compounds 35A-35D may be separately mixed into the polymeric material(s) used to form microneedle 14A (or any and/or all of the microneedles comprising the microneedle array 12) such that the anti-wound healing compound(s) is/are impregnated within the polymeric material forming microneedle 14A. In one embodiment, the at least one anti-wound healing compound(s) 35A-35D may comprise a time-released formulation whereby the anti-wound healing compounds are released at predetermined intervals when in contact with the patient's fluid sample.

Upon insertion into a patient's epidermal tissue, microneedle 14A comes into contact with the patient's fluid sample, for instance, the patient's interstitial fluid (not shown). The patient's fluid sample (not shown) is both in contact with an outer surface 24B of microneedle 14A and an inner surface 24A of microneedle 14A (via the fluid sample flowing into the bore 23 of microneedle 14A through opening 25, or, as discussed above, when the microneedle 14A is formed from a porous polymeric hydrogel, via diffusion through the pores into bore 23 of microneedle 14A). Once microneedle 14A (and the other microneedles comprising the microneedle array 12) is inserted into the patient's epidermal tissue, microneedle 14A is hydrated by the patient's fluid sample (such as the patient's interstitial fluid). This hydration with the patient's fluid sample allows for both the real-time detection of an analyte(s) of interest (for instance, glucose) present in the patient's fluid sample via the analyte binding to analyte sensor(s) 20A-20E and the release of anti-wound healing compounds 35A-35D that prevent, mitigate, and/or eliminate the biofouling process as discussed herein.

Figure 4:
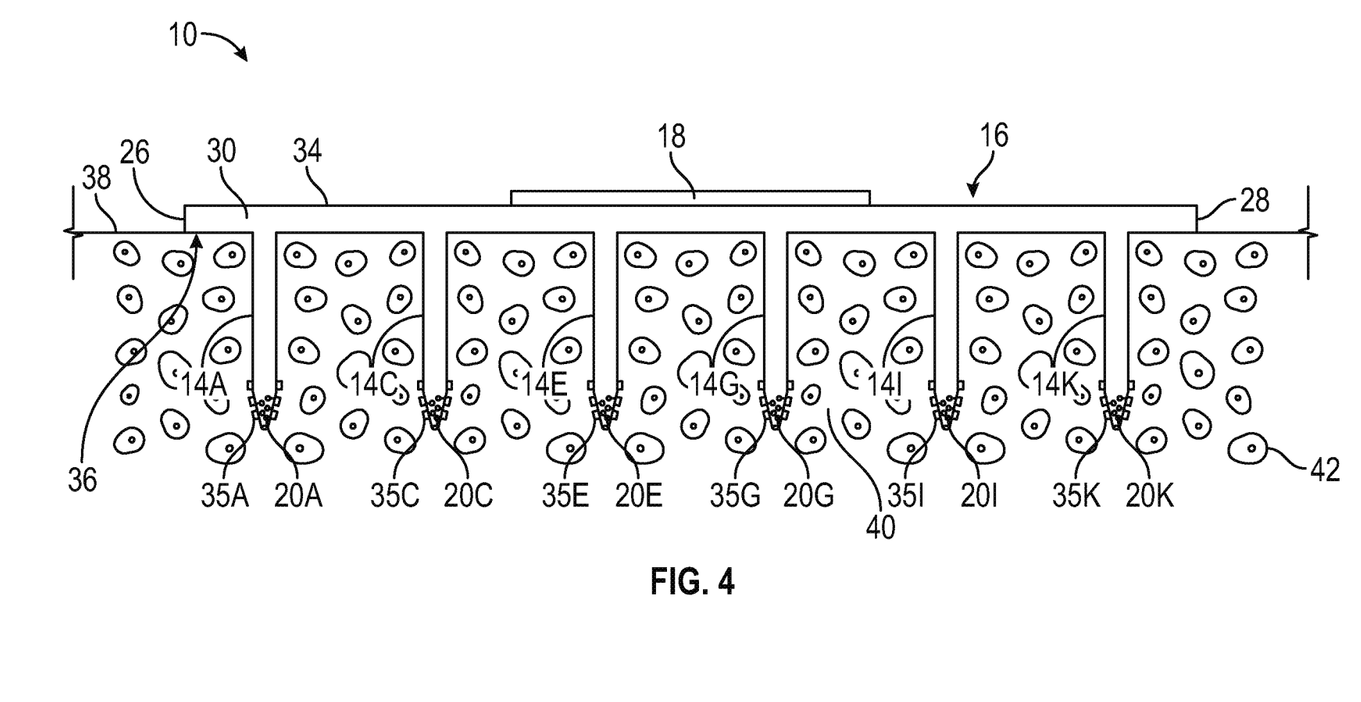
FIG. 4 is a side view of one embodiment of the improved indwelling, wearable biosensor of the presently disclosed and/or claimed inventive concept(s) in which the biosensor is indwelled within the epidermal tissue of a patient and in fluid communication with the patient's fluid sample.

Referring now to FIG. 4, shown therein is one non-limiting embodiment of the improved indwelling, wearable biosensor 10 of the presently disclosed and/or claimed inventive concept(s) in which the biosensor 10 is indwelled within epidermal tissue 38 of a patient and in fluid communication with the patient's fluid sample 40. In this non-limiting embodiment, the indwelling, wearable biosensor 10 comprises: a microneedle array 12 comprising a plurality of microneedles 14A, 14C, 14E, 14G, 14I, 14K (referred to collectively for purposes of simplicity as microneedles 14); a substrate 16 comprising a first end 26, a second end 28, a first side 30, a second side 32 (not shown), a top portion 34, and a bottom portion 36; and a detector 18. Each of the microneedles 14 comprise a plurality of analyte sensor(s) 20A, 20C, 20E, 20G, 20I, and 20K (referred to collectively for purposes of simplicity as analyte sensor(s) 20) and at least one anti-wound healing compound(s) 35A, 35C, 35E, 35G, 35I, and 35K (referred to collectively for purposes of simplicity as at least one anti-wound healing compound(s) 35) associated with the polymeric materials forming the microneedles 14.

The biosensor 10 is applied to a patient's epidermal tissue 38 via pressure, including, without limitation, via pressure applied to the top surface 34 of the substrate 16 and, in one non-limiting embodiment, is held in place via an adhesive present on the bottom surface 36 of the substrate 16. Once applied, the microneedle array 12 pierces the epidermal tissue 38 of the patient thereby bringing the plurality of microneedles 14 into fluid communication with the patient's fluid sample 40, which, in one non-limiting embodiment, is the patient's interstitial fluid. The patient's fluid sample 40 hydrates the plurality of microneedles 14 including both the outer surface(s) and the inner surface(s) (via diffusion of the patient's fluid sample 40 through the openings and into the bores of each microneedle comprising the plurality of microneedles 14). As a result of this hydration, the plurality of anti-wound healing compounds 35 are released which thereby prevent, mitigate, and/or eliminate the biofouling process (such as, by way of example only, by inhibiting or mitigating the inflammation phase of the wound healing process and/or preventing the accumulation and agglomeration of cells 42, proteins, and/or other biological substances around and/or within each microneedle of the plurality of microneedles 14). In addition, the hydration results in the patient's fluid sample 40 being diffused into each microneedle of the plurality of microneedles 14. If the patient's fluid sample 40 contains an analyte(s) of interest (for instance, glucose) (not shown), the analyte(s) of interest associate with the plurality of analyte sensor(s) 20, whereby, when the plurality of analyte sensor(s) 20 comprise at least one fluorophore, the plurality of analyte sensor(s) 20 emit fluorescent signals that are subsequently detected by detector 18 (for instance, by traveling up or through the length of each optically transparent microneedle of the plurality of microneedles 14). The detector 18 then correlates and calculates the concentration(s) based on the intensity of the fluorescent signal(s) received from the plurality of analyte sensor(s) 20. Once correlated and calculated, the detector 18 (via internal circuitry (not shown)) wirelessly transmits the correlated and calculated data to at least one external device(s), including, but not limited to, computer monitors and mobile devices, such as laptops, tablets, and/or cellular phones (not shown). The external device then displays the correlated and calculated data so that a user can interpret, monitor, and develop effective therapeutic plans for treating a patient based on the display of such data on such external device(s).

Referring now to FIG. 5, shown therein is an additional embodiment of the presently disclosed and/or claimed inventive concept(s) in which piezoelectric elements 44A-44L are incorporated into each of the microneedles 14A-14L of the microneedle array 12.

In addition, FIG. 5 illustrates the wireless communication and transmission of correlated and calculated data from a controller 46 of the detector 18 to at least one external device 48, including, without limitation, laptops, cellular phones, tablets, and computers/computer monitors. The transmittance of this data is applicable to any and all embodiments of the presently disclosed and/or claimed inventive concept(s). For instance, after the detector correlates and calculates the concentration of the analyte(s) of interest present in the patient's fluid sample based on the signal(s) received from the previously discussed analyte sensor(s) (for instance, fluorescent signal(s)), this data is then wirelessly transmitted to the at least one external device 48.

In one non-limiting embodiment, each of the microneedles 14A-14L of the microneedle array 12 comprise at least one piezoelectric element(s) 44A-44L. The at least one piezoelectric element(s) 44A-44L detect pressure changes and/or differentials within the each microneedle 14A-14L of the microneedles array 12 (for instance, pressure changes and/or differentials resulting from the blockage or partial blockage of each of the microneedles 14A-14L due to the accumulation or agglomeration of cells, proteins, and/or other biological substances (not shown) resulting from the biofouling process discussed herein). Upon detecting a pressure change and/or differential (represented by ΔP in FIG. 5), an electrical signal is sent to the detector 18 where it is received by a controller 46. The controller 46, following receipt of the electrical signal indicative of a pressure change and/or differential associated with any or all of the microneedles 14A-14L, subsequently delivers an electrical signal (represented by E in FIG. 5) to each of the microneedles 14A-14L of the microneedle array 12 which are received by the at least one piezoelectric element(s) 44A-44L. In response to the receipt of the electrical signal, the at least one piezoelectric element(s) 44A-44L vibrate, the vibration(s) thereby dislodging and removing any cells, proteins, and/or other biological substances that have accumulated or agglomerated on or within each of the microneedles 14A-14L of the microneedle array 12 as a result of biofouling.

While FIG. 5 depicts a single piezoelectric element per each microneedle of the microneedle array 12, it should be readily understood to a person having ordinary skill in the art that each microneedle may comprise more than one piezoelectric element, or, alternatively, only certain of the microneedles 14A-14L may comprise a piezoelectric element. The piezoelectric element(s) 44A-44L may be the same, different, or a combination of same and different composition(s). In addition, rather than sending an electrical signal in response to a received signal indicative of a pressure change and/or differential, the controller 46 of detector 18 may be programmed or pre-programmed to deliver an electrical signal or electrical signals to one, some, or all of the piezoelectric element(s) 44A-44L at regularly scheduled intervals to thereby continuously prevent the accumulation and/or agglomeration of cells, protein(s), and/or other biological substances on or within one, some, or all of the microneedles 14A-14L of the microneedle array 12.

In an alternative non-limiting embodiment, the biosensor 10 may comprise at least one piezoelectric element which is disposed on the top portion 34 of substrate 16. In this embodiment, the detector 18 (via controller 46) is capable of delivering an electrical signal to the at least one piezoelectric element thereby resulting in the vibration of the at least one piezoelectric element. The vibrational signal generated by the at least one piezoelectric element is subsequently received by one, some, or all of microneedles 14A-14L (by way of example only, via rim portions of microneedles 14A-14L present on the top portion 34 of substrate 16 which secure microneedles 14A-14L to the substrate 16) to thereby prevent, mitigate, and/or eliminate the accumulation and/or agglomeration of cells, protein(s), and/or biological substances on or within one, some, or all of the microneedles 14A-14L of the microneedle array 12.

Non-Limiting Examples of the Inventive Concept(s)

An indwelling, wearable biosensor device for the continuous detection and monitoring of at least one analyte in a patient's fluid sample, the device comprising: a microneedle array, the microneedle array comprising a plurality of microneedles constructed of at least one polymeric material, wherein the plurality of microneedles is imbedded in an epidermal tissue of a patient such that the plurality of microneedles is in continuous contact with a fluid sample of a patient, and further wherein at least one surface of each microneedle of the plurality of microneedles comprises at least one anti-wound healing compound which inhibits a wound healing process when the microneedle array is embedded in the epidermal tissue of the patient; a plurality of analyte sensors operatively associated with the polymeric material of each microneedle of the plurality of microneedles, the plurality of analyte sensors generating signals indicative of a concentration of at least one analyte present in the fluid sample of the patient; a substrate having a top portion and a bottom portion, wherein the microneedle array is permanently attached to the bottom portion of the substrate; and a detector, wherein the detector comprises circuitry for receiving the signals generated by the plurality of analyte sensors, calculating the concentration of the at least one analyte present in the fluid sample of the patient, and transmitting the concentration to an external device for diagnosis and evaluation of proposed treatments.

The biosensor device, wherein the polymeric material is polyacrylamide.

The biosensor device, wherein the fluid sample is selected from the group consisting of interstitial fluid and blood.

The biosensor device, wherein the bottom portion of the substrate comprises an adhesive for affixing the substrate to the epidermal tissue of the patient.

The biosensor device, wherein the detector is selected from the group consisting of a microfluorometer, a filter fluorometer or a spectrofluorometer.

The biosensor device, wherein the plurality of analyte sensors comprise at least one fluorophore, wherein the at least one fluorophore is selected from the group consisting of fluorescein, rhodamine, eosin, Oregon Green, Texas Red, coumarin derivatives, cyanine, indocarbocyanine, oxacarbocyanine, thiacarbocyanine, merocyanine, squaraine derivatives, pyridyoxazole, nitrobenzoxadiazole, benzoxadiazole, anthraquinones, pyrene derivatives, Nile Red, Nile Blue, cresyl violet, oxazine, proflavin, acridine orange, acridine yellow, auramine, crystal violet, malachite green, porphyrin, phtalocyanine, bilirubin, boronate, and combinations thereof.

The biosensor device, wherein the at least one analyte present in the fluid sample of the patient is glucose.

The biosensor device, wherein the at least anti-wound healing compound is selected from the group consisting of immunosuppressant compounds, corticosteroids, chitosan, nonsteroidal anti-inflammatory drugs, aspirin, naproxen, ibuprofen, anticoagulant compounds, and combinations thereof.

An indwelling, wearable biosensor device for the continuous detection and monitoring of at least one analyte in a patient's fluid sample, the device comprising: a microneedle array, the microneedle array comprising a plurality of microneedles constructed of at least one polymeric material, wherein the plurality of microneedles is imbedded in an epidermal tissue of a patient such that the plurality of microneedles is in continuous contact with a fluid sample of a patient, and further wherein at least one microneedle of the plurality of microneedles comprises at least one piezoelectric element; a substrate having a top portion and a bottom portion, wherein the microneedle array is permanently attached to the bottom portion of the substrate; and a detector, wherein the detector comprises circuitry for receiving the signals generated by the at least one piezoelectric element, calculating the concentration of the at least one analyte present in the fluid sample of the patient, and transmitting the concentration to an external device for diagnosis and evaluation of proposed treatments, further wherein the detector receives a first electrical signal generated by the at least one piezoelectric element and delivers a second electrical signal to the at least one piezoelectric element resulting in the vibration of the at least one piezoelectric element.

The biosensor device, wherein the polymeric material is polyacrylamide.

The biosensor device, wherein the fluid sample is selected from the group consisting of interstitial fluid and blood.

The biosensor device, wherein the at least one piezoelectric element is selected from the group consisting of quartz, Berlinite, topaz, tourmaline, cane sugar, Rochelle salt, barium titanate, and lead zirconate titanate.

The biosensor device, wherein the bottom portion of the substrate comprises an adhesive for affixing the substrate to the epidermal tissue of the patient.

The biosensor device, wherein the at least one analyte present in the fluid sample of the patient is glucose.

An indwelling, wearable biosensor device for the continuous detection and monitoring of at least one analyte in a patient's fluid sample, the device comprising: a microneedle array, the microneedle array comprising a plurality of microneedles constructed of a polymeric material, the plurality of microneedles comprising at least one calibration microneedle, wherein the plurality of microneedles is imbedded in an epidermal tissue of a patient such that the plurality of microneedles is in continuous contact with a fluid sample of a patient; a plurality of analyte sensors operatively associated with the polymeric material of each microneedle of the plurality of microneedles, the plurality of analyte sensors generating signals in the presence of at least one analyte, the signals being indicative of a concentration of at least one analyte present in the fluid sample of the patient, and further wherein the plurality of analyte sensors operatively associated with the polymeric material of the at least one calibration needle emit a constant signal when exposed to the fluid sample of the patient; a substrate having a top portion and a bottom portion, wherein the microneedle array is permanently attached to the bottom portion of the substrate; and a detector, wherein the detector comprises circuitry for receiving the signals generated by the plurality of analyte sensor(s), calculating the concentration of the at least one analyte present in the fluid sample of the patient, and transmitting the concentration to an external device for diagnosis and evaluation of proposed treatments.

The biosensor device, wherein the polymeric material is polyacrylamide.

The biosensor device, wherein the fluid sample is selected from the group consisting of interstitial fluid and blood.

The biosensor device, wherein the bottom portion of the substrate comprises an adhesive for affixing the substrate to the epidermal tissue of the patient.

The biosensor device, wherein the detector is selected from the group consisting of a microfluorometer, a filter fluorometer or a spectrofluorometer.

The biosensor device, wherein the plurality of analyte sensors comprise at least one fluorophore, wherein the at least one fluorophore is selected from the group consisting of fluorescein, rhodamine, eosin, Oregon Green, Texas Red, coumarin derivatives, cyanine, indocarbocyanine, oxacarbocyanine, thiacarbocyanine, merocyanine, squaraine derivatives, pyridyoxazole, nitrobenzoxadiazole, benzoxadiazole, anthraquinones, pyrene derivatives, Nile Red, Nile Blue, cresyl violet, oxazine, proflavin, acridine orange, acridine yellow, auramine, crystal violet, malachite green, porphyrin, phtalocyanine, bilirubin, boronate, and combinations thereof.

The biosensor device, wherein the at least one analyte present in the fluid sample of the patient is glucose.

Thus, in accordance with the presently disclosed and claimed inventive concept(s), there have been provided devices and methods of an improved indwelling, wearable biosensor that prevents, mitigates, and/or eliminates the effects of biofouling of the biosensor (as well as devices for calibrating the biosensor and methods related thereto). As described herein, the presently disclosed and claimed inventive concept(s) relate to embodiments of improved, indwelling, wearable biosensors, methods of use related thereto, devices and methods for preventing, mitigating, and/or eliminating the effects of biofouling to the biosensor, and devices and methods related to calibration of the biosensor. Such presently disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. An indwelling, wearable biosensor device for the continuous detection and monitoring of at least one analyte in a patient's fluid sample, the device comprising:
    a microneedle array, the microneedle array comprising a plurality of microneedles constructed of at least one polymeric material, wherein the plurality of microneedles is imbedded in an epidermal tissue of a patient such that the plurality of microneedles is in continuous contact with a fluid sample of a patient, and further wherein at least one microneedle of the plurality of microneedles comprises at least one piezoelectric element;
    a plurality of fluorophore sensors, wherein each fluorophore sensor is operatively associated with the at least one polymeric material of at least one microneedle of the plurality of microneedles, wherein each fluorophore sensor emits a fluorescent signal in the presence of at least one analyte that is indicative of a concentration of the at least one analyte in the fluid sample of the patient, and wherein each fluorophore sensor emits a constant signal when exposed to the fluid sample of the patient;
    a substrate having a top portion and a bottom portion, wherein the microneedle array is permanently attached to the bottom portion of the substrate; and
    a detector that receives signals emitted by the plurality of fluorophore sensors for calculating the concentration of the at least one analyte present in the fluid sample of the patient, and transmitting the concentration to an external device for diagnosis and evaluation of proposed treatments, and
    wherein the detector comprises circuitry for receiving the signals generated by the at least one piezoelectric element, and further wherein the detector receives a first electrical signal generated by the at least one piezoelectric element and delivers a second electrical signal to the at least one piezoelectric element resulting in the vibration of the at least one piezoelectric element.

2. The device of claim 1, wherein the at least one polymeric material is polyacrylamide.

3. The device of claim 1, wherein the fluid sample is selected from the group consisting of interstitial fluid and blood.

4. The device of claim 1, wherein the at least one piezoelectric element is selected from the group consisting of quartz, Berlinite, topaz, tourmaline, cane sugar, Rochelle salt, barium titanate, and lead zirconate titanate.

5. The device of claim 1, wherein the bottom portion of the substrate comprises an adhesive for affixing the substrate to the epidermal tissue of the patient.

6. The device of claim 1, wherein the at least one analyte present in the fluid sample of the patient is glucose.

7. The device of claim 1, wherein each fluorophore sensor comprises at least one fluorophore selected from the group consisting of fluorescein, rhodamine, eosin, Oregon Green, Texas Red, coumarin derivatives, cyanine, indocarbocyanine, oxacarbocyanine, thiacarbocyanine, merocyanine, squaraine derivatives, pyridyoxazole, nitrobenzoxadiazole, benzoxadiazole, anthraquinones, pyrene derivatives, Nile Red, Nile Blue, cresyl violet, oxazine, proflavin, acridine orange, acridine yellow, auramine, crystal violet, malachite green, porphyrin, phtalocyanine, bilirubin, boronate, and combinations thereof.

8. The device of claim 1, wherein the detector is selected from the group consisting of a microfluorometer, a filter fluorometer, or a spectrofluorometer.

9. An indwelling, wearable biosensor device for the continuous detection and monitoring of at least one analyte in a patient's fluid sample, the device comprising:
    a microneedle array, the microneedle array comprising a plurality of microneedles constructed of at least one polymeric material, the plurality of microneedles comprising at least one calibration microneedle, wherein the plurality of microneedles is imbedded in an epidermal tissue of a patient such that the plurality of microneedles is in continuous contact with a fluid sample of a patient;
    a plurality of fluorophore sensors, wherein each fluorophore sensor is operatively associated with the at least one polymeric material of at least one microneedle of the plurality of microneedles, wherein each fluorophore sensor emits a fluorescent signal in the presence of at least one analyte that is indicative of a concentration of the at least one analyte present in the fluid sample of the patient, and further wherein each of the plurality of analyte sensors emits a constant signal when exposed to the fluid sample of the patient;

a substrate having a top portion and a bottom portion, wherein the microneedle array is permanently attached to the bottom portion of the substrate; and a detector that receives signals emitted by the plurality of fluorophore sensors for calculating the concentration of the at least one analyte present in the fluid sample of the patient, and transmitting the concentration to an external device for diagnosis and evaluation of proposed treatments.

10. The device of claim 9, wherein the at least one polymeric material is polyacrylamide.

11. The device of claim 9, wherein the fluid sample is selected from the group consisting of interstitial fluid and blood.

12. The device of claim 9, wherein the bottom portion of the substrate comprises an adhesive for affixing the substrate to the epidermal tissue of the patient.

13. The device of claim 9, wherein the detector is selected from the group consisting of a microfluorometer, a filter fluorometer or a spectrofluorometer.

14. The device of claim 9 wherein each fluorophore sensor comprises at least one fluorophore selected from the group consisting of fluorescein, rhodamine, eosin, Oregon Green, Texas Red, coumarin derivatives, cyanine, indocarbocyanine, oxacarbocyanine, thiacarbocyanine, merocyanine, squaraine derivatives, pyridyoxazole, nitrobenzoxadiazole, benzoxadiazole, anthraquinones, pyrene derivatives, Nile Red, Nile Blue, cresyl violet, oxazine, proflavin, acridine orange, acridine yellow, auramine, crystal violet, malachite green, porphyrin, phtalocyanine, bilirubin, boronate, and combinations thereof.

15. The device of claim 9, wherein the at least one analyte present in the fluid sample of the patient is glucose.

* * * * *